United States Patent [19]

Takami et al.

[11] Patent Number: 4,656,863

[45] Date of Patent: Apr. 14, 1987

[54] GAS SENSOR

[75] Inventors: Akio Takami; Toshitaka Matsuura; Nobuo Kawai, all of Nagoya, Japan

[73] Assignee: NGK Spark Plug Co., Ltd., Nagoya, Japan

[21] Appl. No.: 769,715

[22] Filed: Aug. 27, 1985

[30] Foreign Application Priority Data

Sep. 3, 1984 [JP] Japan ................................ 59-182559

[51] Int. Cl.$^4$ ........................................... G01N 27/12
[52] U.S. Cl. .......................................... 73/23; 338/34
[58] Field of Search ................... 73/23, 27 R; 338/34; 340/634; 422/98

[56] References Cited

U.S. PATENT DOCUMENTS

4,414,531 11/1983 Novak ................................ 73/27 R

Primary Examiner—Stephen A. Kreitman
Attorney, Agent, or Firm—Fleit, Jacobson, Cohn & Price

[57] ABSTRACT

A gas sensor has an elongated planar ceramic substrate carrying a gas-sensitive layer at one end thereof, and a ceramic layer overlaid on the substrate with a setback from the gas-sensitive layer so as to form a staircase-like step on the substrate, the setback edge surface of the ceramic layer being non-linear in the width direction of the substrate but preferably perpendicular to the plane of substrate.

12 Claims, 34 Drawing Figures

FIG_3A

FIG_3B

FIG_3C

FIG_3D

FIG_18A

FIG_18B

FIG. 19

GAS SENSOR

BACKGROUND OF THE INVENTION

1. Field of the Invention

This invention relates to a gas sensor, and more particularly to a shock-resistive gas sensor for detecting a gaseous ingredient or its concentration.

2. Related Art Statement

It has been known to detect the presence and concentration of a gas in air by a gas sensor which uses a gas-sensitive element made of an oxide semiconductor, such as tin oxide ($SnO_2$), zinc oxide (ZnO), titania ($TiO_2$), cobalt oxide (CoO), and the like, whose electric resistance varies upon exposure to the gas. To simplify the structure of such gas-sensitive element for improving the productivity thereof, the so-called hybrid techniques has been developed; for instance, by printing both the gas-sensitive element and electrodes therefor in the form of thick films on an electrically insulating ceramic substrate.

It is generally difficult to mount directly the ceramic substrate carrying the gas-sensitive element onto a device in a combustion environment or in an exhaust gas duct for sensing a specific gas therein.

To hold such a gas sensor in position for actual measurement, it has been practiced heretofore to put it in a housing which can be readily fixed at a location for detecting the object gas. However, certain difficulties have been experienced: for instance, that the gas sensor with the gas-sensitive element formed on the ceramic substrate has smooth surface with little undulations and it has been difficult to determine which part of the sensor be fixed to the housing with or without a spacer therebetween; and that, when a spacer is used between the housing and the gas sensor, the spacer tends to contact the gas-sensitive element and no harm to it during the assemblying process, because the gas-sensitive element projects from the substrate for sensing the gas while the spacer keeps rather tight contact with the substrate for ensuring the secure holding.

To overcome such difficulties, it has been proposed to form a staircase-like step on the substrate carrying the gas-sensitive element, so that the substrate is held in position by engaging the staircase-like step against a holder or spacer in the housing. For instance, the gas-sensitive element is formed at a tip portion of an elongated substrate while the staircase-like step is formed at root portion of such elongated substrate, whereby the root portion of the substrate is firmly held in position within the housing so as to extend the gas-sensitive element into the atmosphere to be measured. The root portion may be fastened to the housing by using suitable fillers or the like. The housing holding the substrate with such staircase-like step can be easy mounted on the device where the gas is to be sensed. However, the staircase-like step of the substrate has a shortcoming in that it is rather weak against mechanical shock, such as impact during transportation or shock due to inadvertent dropping, and rather frequent breakage has been experienced in the substrate of such gas sensor due to mechanical shocks during handling.

SUMMARY OF THE INVENTION

Therefore, an object of the invention is to obviate the above-mentioned difficulties of the prior art by providing an improved gas sensor which has a high strength against mechanical shock and yet is easy to mount on a housing without any risk of harming the gas-sensitive element thereof during assembling. The structure of the gas sensor of the invention is such that, when a spacer is used between the housing and the gas sensor, which portion of the gas sensor be held by the spacer is easily determined and the risk of harming the gas-sensitive element by the spacer during the assembling is minimized.

Another object of the invention is to provide a shock-resistive gas sensor having a gas-sensitive layer formed on a ceramic substrate, which gas sensor is easily mountable onto a housing while ensuring both correct positioning by using a spacer and protection of the gas-sensitive layer against damage due to inadvertent contact thereof with the spacer during the mounting.

To fulfill the above object, a gas sensor according to the invention uses a combination of an elongated planar ceramic substrate carrying a gas-sensitive layer formed at one longitudinal end thereof and a ceramic layer integrally overlaid on the ceramic substrate with a non-linear setback from the gas-sensitive layer. Accordingly, a staircase-like step is formed on the ceramic substrate by the setback edge surface of the ceramic layer. When the gas sensor is mounted on a housing by using a spacer between the housing wall and the gas sensor, this staircase-like step serves as positioning step, so that correct positioning of the gas sensor can be ensured.

In the gas sensor of the invention, the staircase-like step of the ceramic layer is non-linearly bent in the width direction of the ceramic substrate so that at least one portion of such step extends toward the gas-sensitive layer, while leaving a space between the extended end of the step and the gas-sensitive layer. Thus, the scope of the invention excludes a staircase-like step which extends linearly in the width direction of the elongated ceramic substrate. For instance, only the central portion or opposite end portions of the staircase-like step of the ceramic layer may extend toward the gas-sensitive layer.

As compared with the linear edge in the width direction of the elongated substrate, the curved edge surface of the ceramic layer is effective in preventing stress concentration when a mechanical impact is applied thereto for instance by dropping. Whereby, the substrate with the thus curved staircase-like step has a high strength against mechanical shock. The above extended portion of the staircase-like step of the ceramic layer provides for engagement of the gas sensor with a spacer between the housing and the gas sensor so as to facilitate correct positioning.

In another embodiment of the invention, a protective staircase-like step is formed on the elongated planar ceramic substrate, in addition to the above-mentioned staircase-like step for positioning. More particularly, a front ceramic layer is integrally overlaid on the ceramic substrate in the proximity of but with a setback from the gas-sensitive layer, so that the setback edge surface of the front ceramic layer forms a protective staircase-like step on the ceramic substrate. The height of the protective staircase-like step from a boundary surface between the ceramic substrate and the front ceramic layer is higher than the thickness of the gas-sensitive layer from the above boundary surface, so that the protective staircase-like step prevents the gas-sensitive layer from being directly touched by the spacer or the like during assembling.

A thick rear ceramic layer is integrally overlaid on the ceramic substrate while setting back a front edge surface of the rear ceramic layer from the above-mentioned protective staircase-like step, so that the setback front edge surface of the rear ceramic layer forms a positioning staircase-like step on the ceramic substrate. The height of the positioning staircase-like step is higher than the protective staircase-like step relative to the above boundary surface, and the positioning staircase-like step formed of the front edge surface of the rear ceramic layer is also curved in the width direction of the ceramic substrate with at least one portion extending toward the gas-sensitive layer. Whereby, the ceramic substrate with the positioning staircase-like step formed thereon has a high strength against mechanical shock.

The protective staircase-like step and the positioning staircase-like step may be formed by overlaying two ceramic layers on the ceramic substrate one over the other. For instance, in another embodiment of the invention, a first ceramic layer is integrally overlaid on the ceramic substrate of the above type with a setback from the gas-sensitive layer so as to form a protective staircase-like step on the ceramic substrate by the setback edge surface of the first ceramic layer. The height of the protective staircase-like step from a boundary surface between the ceramic substrate and the first ceramic layer is higher than the thickness of the gas-sensitive layer from the above boundary surface.

A second ceramic layer is integrally overlaid on the first ceramic layer with a setback from the protective staircase-like step, so as to form a positioning staircase-like step on the first ceramic layer by the setback edge surface of the second ceramic layer. The positioning staircase-like step is also curved in the width direction of the ceramic substrate with at least one portion exteding toward the gas-sensitive layer. Whereby, the ceramic substrate with the positioning staircase-like step formed thereon has a high strength against mechanical shock.

In another embodiment of the invention, a heater layer is secured to the ceramic substrate so as to heat the gas-sensitive layer.

BRIEF DESCRIPTION OF THE DRAWINGS

For a better understanding of the invention, reference is made to the accompanying drawings, in which.

Through different views of the drawings, 1 is a gas sensor, 1a is a gas-sensitive layer, 1b is a positioning staircase-like step, 1c is a protective staircase-like step, 2 is a housing body hardware, 3 is a protector, 4 is an inner cylinder, 5 is a holder-spacer, 6 is filler powder, 7 is glass seal, 8, 9, 10 are terminals, 11 is silicone rubber, 12 is an outer cylinder, 13 is a connector, 14 is a thick substrate green sheet, 15, 16 are electrodes, 17 is a heater layer, 18, 19, 20 are terminal patterns 21, 22, 23 are platinum lead wires, 24 is a thin substrate green sheet, 25 is an opening, 26 is a ceramic layer, 27 is a notch, 28 is a projection, 29 is a recess, 31 is a gas-sensitive layer, 32 is a ceramic substrate, 33 is a firt ceramic layer, 34 is a second ceramic layer, 40 is a gas sensor, 41 is gas-sensitive material, 42 is a housing body hardware, 43 is a protector, 44 is an inner cylinder, 45 is a spacer, 46 is filler powder, 47 is glass seal, 48 is a gasket, 49 is an outer cylinder, 50 is a sealing, 51 through 53 are lead wires, 54 through 56 are compressible connectors, 61 through 63 are terminals, 70 is a ceramic substrate green sheet, 71 is a ceramic cover green sheet, 72 is a first ceramic layer green sheet, 73 is a second ceramic layer green sheet, 74 and 75 are electrodes, 76 is a heater layer, 77 through 79 are end portions, 81 through 83 are platinum lead wires, 85 is an opening, and 86 is a central notch.

DESCRIPTION OF THE PREFERRED EMBODIMENTS

Figure 1:
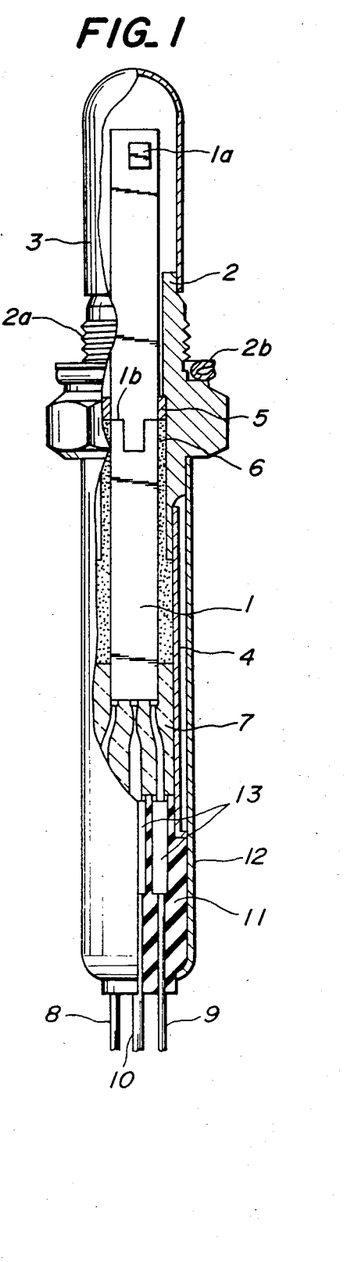
FIG. 1 is a partially cutaway elevation of an oxygen detector having an oxygen sensor embodying the invention mounted therein.
Figure 2:
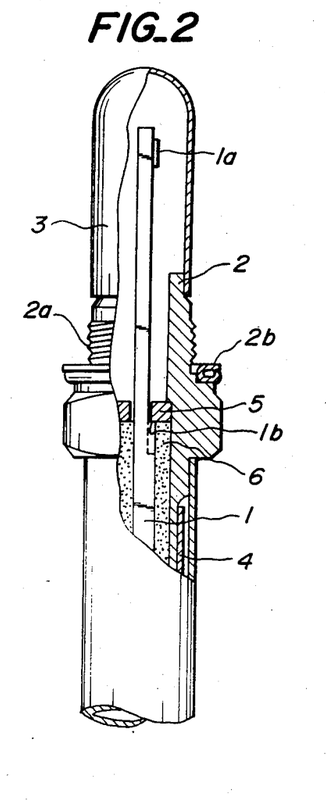
FIG. 2 is a partially cutaway side view of the oxygen detector of FIG. 1 showing the side view of its oxygen sensor.

The gas sensor of the invention will now be described in detail by referring to embodiments which are applicable to oxygen sensors. In FIG. 1 showing an elevation of a gas sensor 1 as incorporated in an oxygen detector and FIG. 2 showing a side view thereof, a gas-sensitive layer 1a is mounted on an elongated planar substrate. The gas sensor 1 is mounted on a housing body hardware 2, and the gas-sensitive layer 1a is guarded by a protector 3, while the root portion of the gas sensor 1 opposite to the gas-sensitive layer 1a is placed in an inner cylinder 4. A holder-spacer 5 is disposed between the gas sensor 1 and the housing body hardware 2 so as to keep the gas sensor 1 in position.

The housing body hardware 2 has a threaded leg 2a for mounting the oxygen detector onto an exhaust gas system from an internal combustion engine (not shown), so that the gas-sensitive layer 1a in the protector 3 is exposed to the atmosphere being measured. A gasket 2b is provided to seal the protector side of the gas detector.

Figure 19:
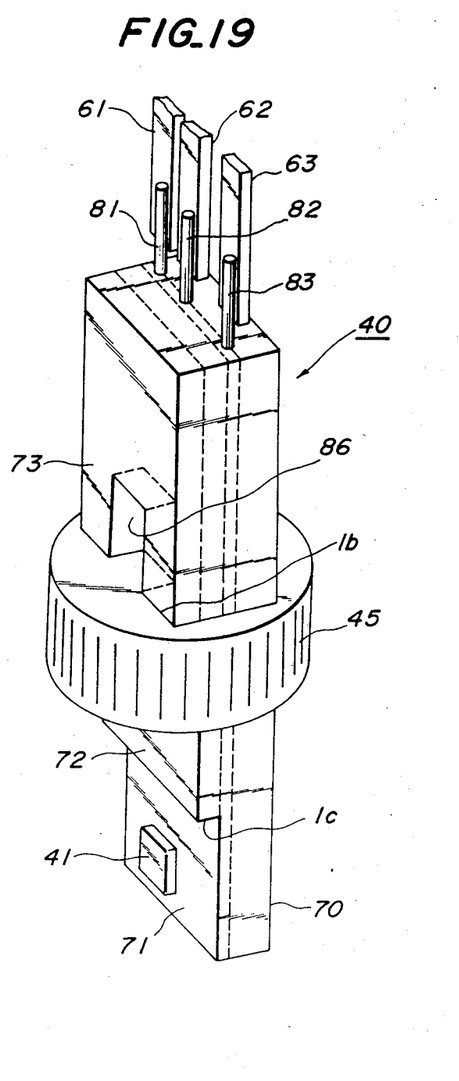
FIG. 19 is a schematic perspective view of the gas sensor of the invention with a spacer mounted thereon.

Referring to FIGS. 1 and 2, the gas sensor 1 has a staircase-like step 1b which engages one end surface of the holder-spacer 5 (see spacer 45 of FIG. 19). Since the spacer-holder 5 is firmly held by the housing body hardware 2, the above engagement of the staircase-like step 1b with the spacer-holder 5 determines the position of the gas-sensitive layer 1a in the protector 3. According to a feature of the invention, the staircase-like step 1b is curved in the width direction of the substrate of the gas sensor 1, so that in the case of FIG. 1 only opposite end portions of the staircase-like step 1b engages the spacer-holder 5 and the central portion thereof is recessed.

The root portion of the gas sensor 1 opposite to the end carrying the gas-sensitive layer 1a is inserted in the inner cylinder 4 and fastened thereto by filler powder 6 and possibly with glass seal 7. Inner ends of lead wires from the terminals 8, 9, and 10 of the gas sensor 1 are held by the housing body hardware 2 and the inner cylinder 4 as an integral part thereof, and outer ends thereof are protected by an outer cylinder 12 while being insulated by silicone rubber 11.

The filler powder 16 is preferably a powder mixture consisting of talc and glass at a ratio of 1:1. The glass seal 17 is preferably made of glass with a low melting point. In FIG. 1, the terminals 8, 9, and 10 are joined to the inside circuit of the gas sensor 1 by connectors 13.

FIG. 3A through FIG. 4D show a process in which the illustrated embodiment of the gas sensor 1 of the invention in FIG. 1 was prepared.

A thick substrate green sheet 14 with a thickness 1 mm and a thin substrate green sheet 24 with a thickness 0.2 mm were made in the following manner: Namely, 100 parts by weight of powder mixture was prepared by mixing 92% by weight (wt%) of alumina ($Al_2O_3$) with a mean diameter of 1.5 $\mu$m, 4 wt% of silica ($SiO_2$), 2 wt% of calcia ($CaO_2$), and 2 wt% of magnesia (MgO); 12 parts by weight of butyral resin and 6 parts by weight of dibutyl phthalate (DBP) were added to the 100 parts by weight of the powder mixture; a slurry was made by mixing the powder mixture after the above addition in an organic solvent; and the green sheets 14 and 24 were formed from the slurry by using a doctor blade while adjusting their thicknesses as specified above.

Figure 3A:
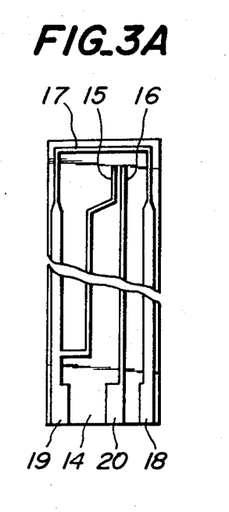
FIG. 3A through FIG. 3D are explanatory diagrams showing different steps in a process for making the gas sensor of the invention.
Figure 3B:
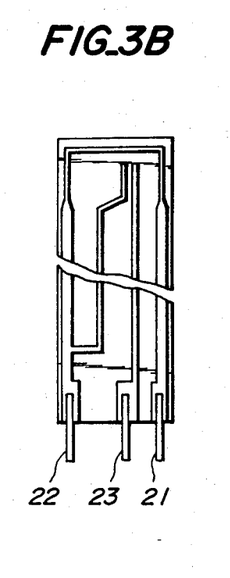

Electrically conductive layers 15 through 20 were printed in the form of thick film patterns as shown in FIG. 3A, by using a platinum paste made by adding 7% of alumina ($Al_2O_3$) based on the amount of platinum. Of such conductive layers, electrodes 15 and 16 were for measuring the electric resistance of the above-mentioned gas-sensitive layer 1a, and a heater layer 17 was for heating the gas-sensitive layer 1a. End portions 18 through 20 were for applying an electric current to the heater layer 17 and extracting the output signal from the gas-sensitive layer 1a. Thereafter, platinum lead wires 21 through 23 with an outer diameter of 0.2 mm were disposed on the end portions 18 through 20 of the patterns respectively, as shown in FIG. 3B.

An opening 25 was bored, for instance by punching, through the thin substrate green sheet 24 at a position corresponding to the gas-sensitive layer 1a, and then the thin substrate green sheet 24 with the opening 25 thus bored was overlaid in position on the thick substrate green sheet 14 so as to cover the entire pattern-printed surface of the latter sheet.

Figure 3C:
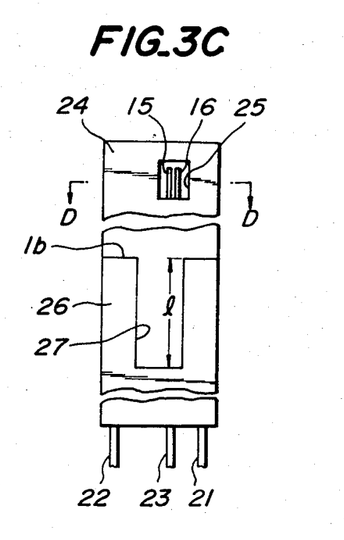
Figure 3D:
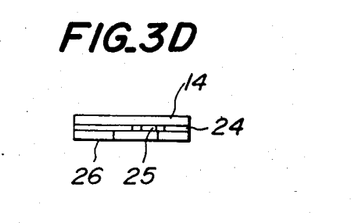

A green sheet for a ceramic layer 26 was prepared in the same manner as that of the above-mentioned green sheets 14 and 24, and it was overlaid on the thin substrate green sheet 24 as shown in FIGS. 3C and 3D. The thickness of the ceramic layer 26 was selected to be suitable for above-mentioned staircase-like step 1b. In the embodiment of the invention as shown in FIG. 3C, the staircase-like step 1b had a notch 27 with a depth 1.

Thus, a laminate body was formed by the above disposing of the conductors 15 through 20 on the thick green sheet 14 and the overlaying of the thin green sheet 24 and the other green sheet for the ceramic layer 26 thereon, and the body thus formed was fired, for instance, at 1,550° C. for two hours in air.

A gas-sensitive layer 1a was deposited on the electrodes 15 and 16 of the fired ceramic substrate through the opening 25 by a conventional method. In the illustrated embodiment, to this end, a titania paste was prepared in the following manner; namely, 5 mole parts of platinum black was mixed in 100 mole parts of titania ($TiO_2$) powder having a mean diameter of 1.2 $\mu$m; 3 wt% of ethyl cellulose based on the total of the powder mixture was added therein; and the mixture thus prepared was further mixed in BUTYL CARBITOL (a merchandise mark of 2-(2)-butoxy ethoxy:ethanol) while controlling its viscosity so as to produce the titania paste having a viscosity of 200 poise, a thick film of this titania paste was printed in the opening 25. The thick film thus printed was fired at 1,200° C. in air.

Figures 4A, 4B, 4C, 4D, 4E, 4F:
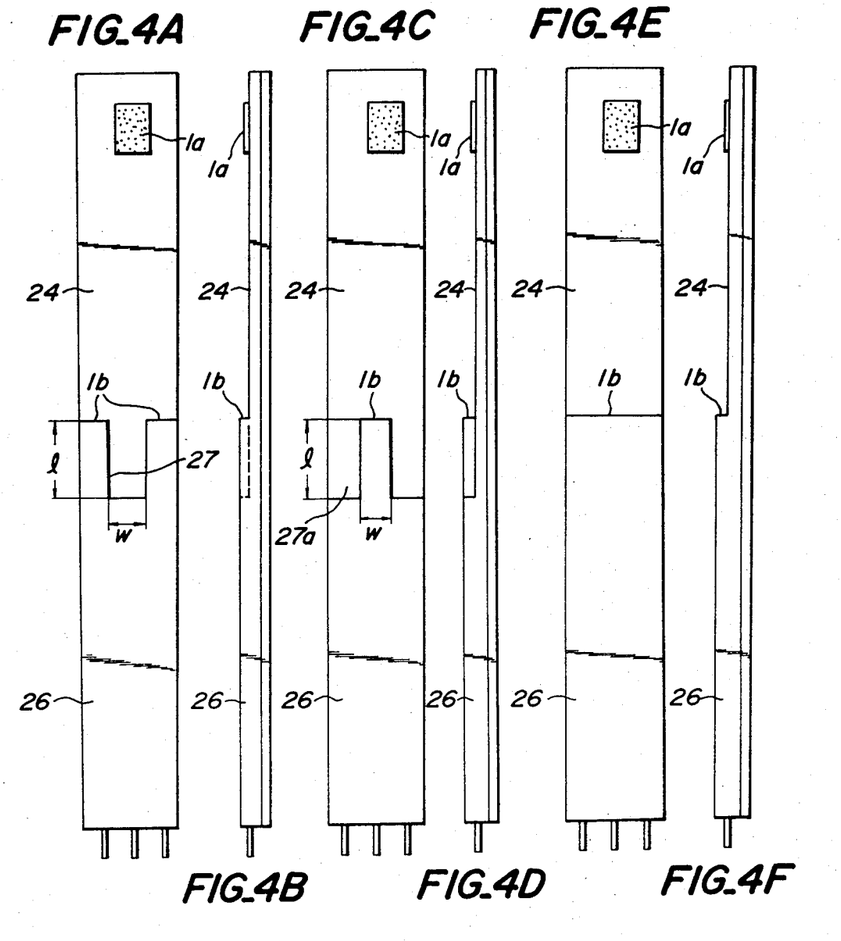
FIG. 4A through FIG. 4F are diagrammatic illustrations of gas sensors which are tested in the experiments described herein.

FIG. 4A shows a plan view of the sample of the gas sensor 1 of the invention thus prepared, and FIG. 4B shows a side view thereof. FIG. 4C shows a plan view of another embodiment of the invention which is similar to that of FIG. 4A except that the staircase-like step 1b had notches 27a at opposite ends thereof so that such step 1b came in contact with the holder-spacer 5 only at the central portion thereof. FIG. 4D shows the side view of the embodiment of FIG. 4C.

The samples of the gas sensor 1 of the invention thus prepared were mounted on the housing body hardwares 2 while bringing only the central portion or only the opposite end portions of the staircase-like steps 1b thereof in contact with the holder-spacer 5, and the samples were fastened to the housing body hardwares 2 by placing the root portions of the gas sensors 1 in the inner cylinders 4 and pouring the filling powder 6 and glass seal 7, such as glass frit with a low melting point, into the inner cylinders 4 and the hardwares 2. The sealing by the glass seal 7 was effected by heating at 530° C. for 15 minutes.

The inventors confirmed through experiments that the staircase-like steps 1b, which were not linear over the entire width of the substrate of the gas sensor 1 but curved in the width direction thereof, provided a high strength against mechanical shock while ensuring reliable positioning by their contact with the holder-spacer 5 in the housing body hardware 2.

Experiments

Two type samples of the gas sensor of the invention, namely 210 pieces of type A sample with a central notch 27 in the staircase-like step 1b as shown in FIG. 4A and 210 pieces of type B sample with opposite end notches 27a in the staircase-like step 1b as shown in FIG. 4C, were prepared. In the samples of the invention, the ceramic substrate of the gas sensor 1 had a width 5 mm, a length 48 mm, a tip thickness 1.5 mm, and root end (fixed end) thickness 2.0 mm. Each central notch 27 of the type A sample had a width w 2 mm and a depth 1 4 mm (for symbols, see FIG. 3C), each notch 27a of the type B sample had a depth 1 4 mm so as to leave the central projection with a width w 2 mm. For reference, 210 pieces of type C sample with a straight staircase-like step 1b as shown in FIGS. 4E and 4F were prepared. The gas sensor samples were assembled in the form of test specimens.

Each test specimen was held 1 m above a concrete floor while holding its gas sensor horizontal, and then the test specimen was dropped onto the concrete floor from the height 1 m. The strength of each test specimen was evaluated by checking the presence and absence of breakage in the substrate of the gas sensor 1 therein after the above dropping test. It was found that all the breakages occurred at the staircase-like steps 1b. The result is shown in Table 1.

TABLE 1

| Specimen type | Number of drops before breakage | | Invention or reference |
|---|---|---|---|
| | Average number | Minimum | |
| A | 32 | 3 | Invention |
| B | 40 | 8 | " |
| C | 8.2 | 1 | Reference |

The result of the experiments as shown in Table 1 proved that the strength of the gas sensor of the invention had been improved by a factor 3 to 8 times as compared with that of the reference structure.

Further experiments were made by preparing two kinds of additional samples; namely one kind samples made by providing the staircase-like step 1b with a central notch 27 as shown in FIG. 4A on opposite surfaces of each substrate of the gas sensor 1; and another kind samples made by providing the staircase-like step 1b with a central notch 27 as shown in FIG. 4A and staircase-like step 1b with opposite end notches 27a as shown in FIG. 4C on opposite surfaces of each substrate of the gas sensor 1. The samples of both two kinds proved to have an excellent strength against mechanical shock.

Third kind of additional samples were prepared by providing a limited step on the gas sensor 1 which step corresponded to the central projection of the staircase-like step 1b after removing the opposite end notches 27a as shown in FIG. 4C. The third kind samples also proved to have an excellent shock-resistivity.

Figures 5, 6:
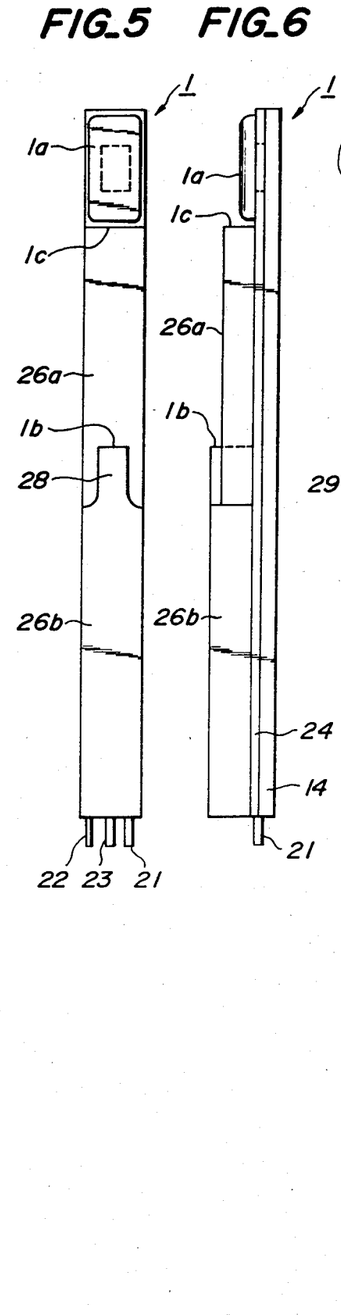
FIG. 5 and FIG. 6 are a plan view and a side view of another embodiment of the invention.
Figure 7:
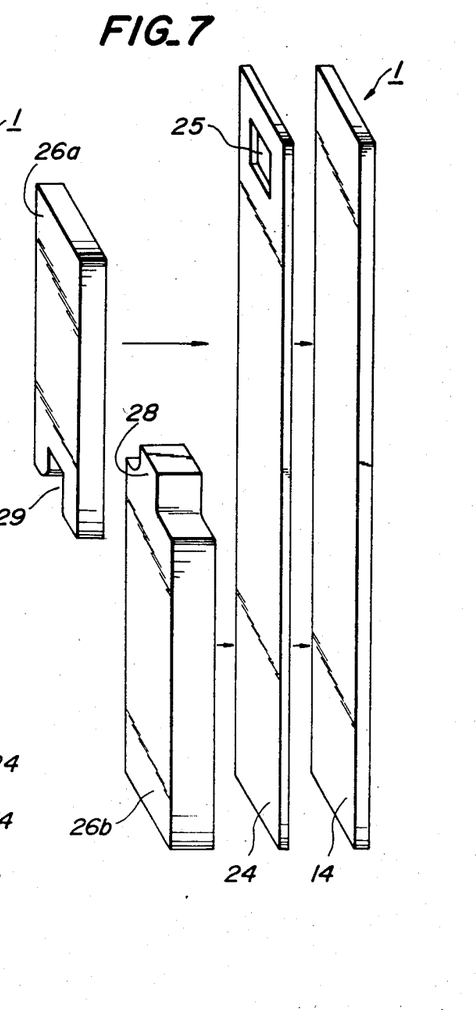
FIG. 7 is an exploded view showing the relationship among different ceramic green sheets in the embodiment of FIG. 5.

FIG. 5 shows another embodiment of the gas sensor according to the invention, and FIGS. 6 and 7 show a side view and an exploded view of this embodiment. For simplicity, FIG. 7 shows only the relationship among the ceramic sheets in the gas sensor 1. A protective staircase-like step 1c is formed by overlaying a front ceramic layer 26a on the substrate of the gas sensor 1. The height of the protective staircase-like step 1c from the boundary surface between the substrate and the front ceramic layer 26a is higher than the thickness of the gas-sensitive layer 1a from that boundary surface. The protective staircase-like step 1c with such height protects the gas-sensitive layer 1a against scratching when the layer 1a is passed through a hole of the holder-spacer 5 for mounting and positioning of the gas sensor 1 thereon.

In the embodiment of FIG. 5, the above-mentioned staircase-like step 1b for positioning is formed by overlaying a rear ceramic layer 26b on the substrate of the gas sensor 1 at a position next to that end of the front ceramic layer 26a which end is opposite to the end facing the protective staircase-like step 1c. The rear ceramic layer 26b is thicker than the front ceramic layer 26a, so that the desired step 1b is formed by the height difference therebetween. In the embodiment of FIG. 5, the rear ceramic layer 26b has a projection 28 which fits in a mating recess 28 provided on the front ceramic layer 26a. Whereby, the positioning staircase-like step 1b becomes curved in the width direction of the substrate of the gas sensor 1.

Figure 8:
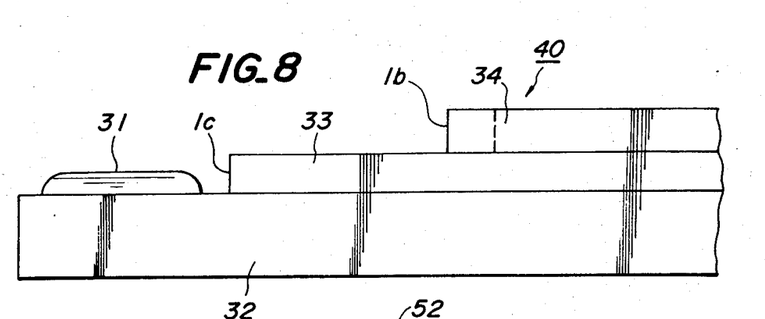
FIG. 8 is a schematic partial side view showing the relationship among different layers in a gas sensor according to the invention.

Referring to FIG. 8, an essential feature of the gas sensor 40 of the invention is in that its gas-sensitive layer 31 is mounted at one end of an elongated planar ceramic substrate 32 so as to be protected by a protective staircase-like step 1c and to be held in position by a non-linear positioning staircase-like step 1b. More particularly, a first ceramic layer 33 and a second ceramic layer 34 are overlaid on the substrate 32 while providing successive setbacks on the ceramic layers 33 and 34 relative to the above-mentioned one end of the substrate 32. Whereby, a protective staircase-like step 1c is formed so as to face the gas-sensitive layer 31. In the structure according to the invention, the first ceramic layer 33 must be thicker than the height of the gas-sensitive layer 31 from that surface of the substrate 32 which adjoins the first ceramic layer 33. The setback edge surface of the second ceramic layer 34 defines the non-linear positioning staircase-like step 1b as will be described hereinafter.

Figure 9:
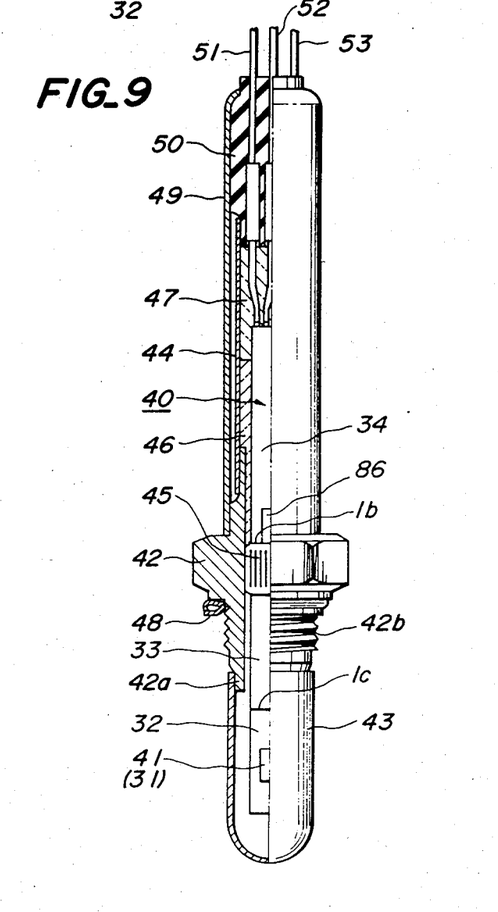
FIG. 9 is a partially cutaway overall side view of an oxygen detector which carries an oxygen sensor embodying the invention mounted therein.

As can be seen from FIG. 9, when a spacer 45 is used to separate the gas sensor 40 from the inside surface of a housing body hardware 42 (FIG. 9), such spacer 45 acts to hold the gas sensor 40 in position by engaging with the positioning staircase-like step 1b with the central notch 86 of the sensor 40 between the first ceramic layer 33 and the second ceramic layer 34. At the same time, the inside surface of the spacer 45 is prevented from coming into direct contact with the gas-sensitive layer 31, because the first ceramic layer 33 is thicker than the height of the gas-sensitive layer 31 above the substrate 32. Thus, correct positioning of the gas sensor 40 in the housing body hardware 42 is ensured, and at the same time the risk of harming the gas-sensitive layer 31 by direct contact of the spacer 45 therewith is substantially eliminated.

In FIG. 9, showing a partially cutaway overall side view of an oxygen detector, a gas sensor 40 of the invention, in the form of an oxygen sensor, has a gas-sensitive layer 41 formed on a ceramic substrate. The gas sensor 40 of this embodiment detects the oxygen concentration of a gas being monitored. A cylindrical housing body hardware 42, which is mountable on an internal combustion engine, houses the gas sensor 40 therein. A protector 43 is coupled to the engine-side end 42a of the housing body hardware 42, so as to protect the gas sensor 40. The gas sensor 40 is held by an inner cylinder 44 with a spacer 45 inserted therebetween, which inner cylinder 44 is carried by the housing body hardware 42. Filler powder 46 and glass seal 47 are stuffed between the gas sensor 40 and the inner cylinder 44, so as to keep the gas sensor 40 in position. To facilitate the mounting of the oxygen detector to an engine (not shown), the housing body hardware 42 has a threaded portion 42b. Thus, the oxygen detector can be screwed to the engine with a gasket 48 disposed between the housing body hardware 42 and the screwed portion of engine wall, so as to prevent engine exhaust gas from leaking through the screwed portion.

The filler powder 46, which is preferably a powder mixture consisting of talc and glass at a ratio of 1:1, acts to fix the gas sensor 40 in position within the inner cylinder 44. The glass seal 47 stuffed in the inner cylinder 44, which seal is preferably made of glass with a low melting point, acts to prevent the gas being monitored from leaking and to protect terminals of the gas sensor 40. To this end, the glass seal 47 covers and holds both a part of the gas sensor 40 and joints of the terminals with platinum lead wires to be described hereinafter.

Figure 10:
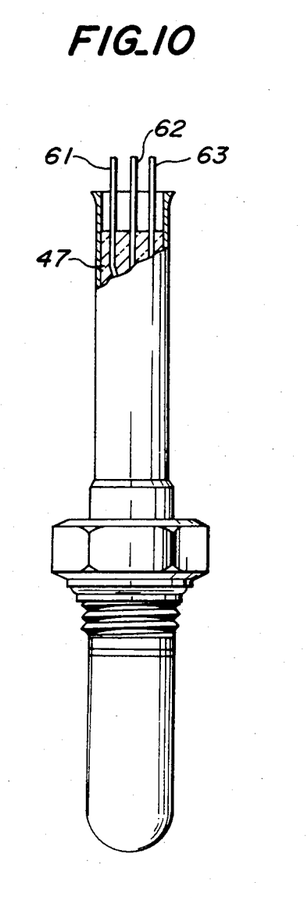
FIG. 10 is a partially cutaway side view of an inner cylinder of the oxygen detector, showing terminals extending outward from a glass seal of the inner cylinder.
Figure 11:
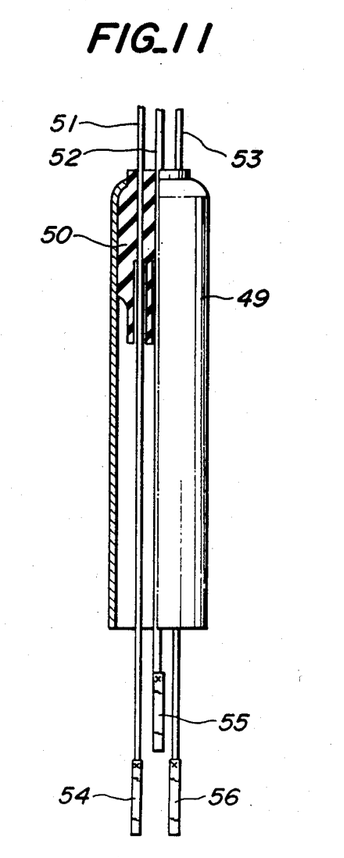
FIG. 11 is a partially cutaway side view of an outer cylinder of the oxygen detector, showing the manner in which one end of the outer cylinder is closed by a sealing before it is coupled with the inner cylinder.

An outer cylinder 49 is coupled to the housing body hardware 42 so as to cover the inner cylinder 44. A sealing 50 made of silicone rubber is stuffed in the outer cylinder 49 at the upper end thereof as shown in FIG. 11, so as to protect and insulate both outgoing lead wires 51 through 53 and their joints with the terminals 61 through 63 of the gas sensor 40 projecting from the glass seal 47 as shown in FIGS. 9 and 10. To facilitate the joining of the lead wires 51 through 53 with the terminals 61 through 63, the sealing 50 and the lead wires 51 through 53 may be placed in the inside of the outer cylinder 49 beforehand, and compressible connectors 54 through 56 may be joined to the inner ends of the lead wires 51 through 53 respectively, as shown in FIG. 11. Then, the terminals 61 through 63 of the gas sensor 40 may be joined to the other ends of the connectors 54 through 56 respectively.

The inventors prepared a sample of the gas sensor 40 by a process as shown in the plan views of FIG. 12A through FIG. 17A. FIG. 12B through FIG. 19B show sections taken along the lines with arrows B in FIG. 12A through FIG. 19A respectively. For clarity of the process of such preparation, the scale of the drawings of the gas sensor 40 in FIG. 12A through FIG. 19A is different from that of the above referred gas sensor 40 in FIG. 9 and from those of FIG. 18A and FIG. 19 to be explained later.

Figures 12A, 12B, 13A, 13B, 14A, 14B, 15A, 15B, 16A, 16B:
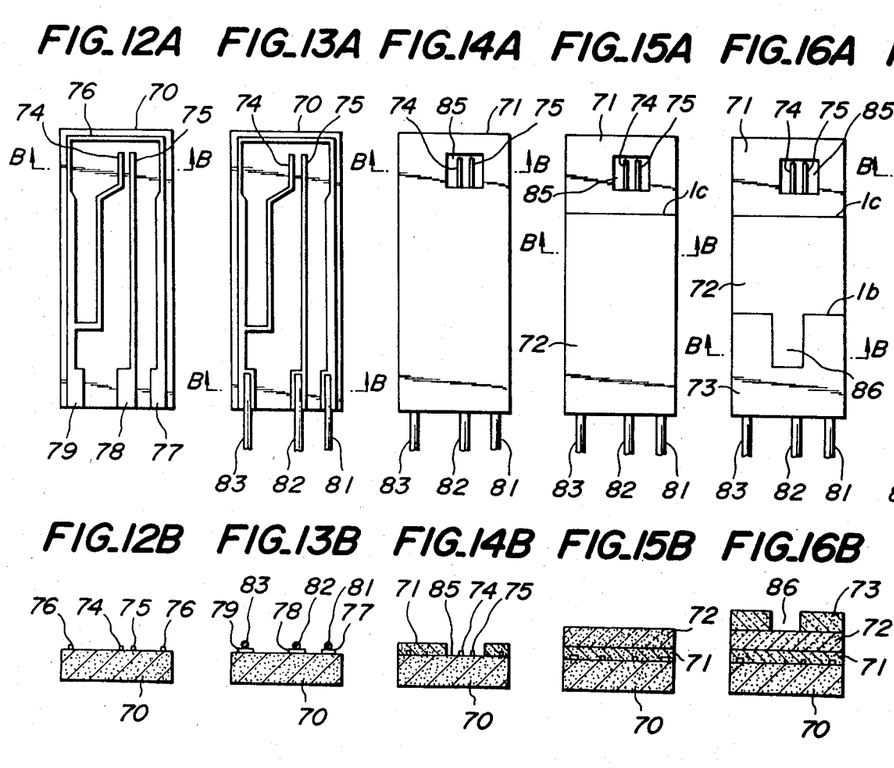
FIG. 12A, FIG. 13A, FIG. 14A, FIG. 15A, FIG. 16A and FIG. 17A are schematic plan views, showing the process in which a gas sensor of the invention is assembled.
FIG. 12B, FIG. 13B, FIG. 14B, FIG. 15B, FIG. 16B and FIG. 17B are sectional views taken along the lines with arrows B in FIG. 12A, FIG. 13A, FIG. 14A, FIG. 15A, FIG. 16A and FIG. 17A, respectively.

A ceramic substrate green sheet 70, a ceramic cover green sheet 71, a first ceramic layer green sheet 72, and a second ceramic layer green sheet 73 having an edge with a central notch as shown in FIG. 16A were formed in the following manner: Namely, 100 parts by weight of powder mixture was prepared by mixing 92% by weight (wt%) of alumina ($Al_2O_3$) with a mean diameter of 1.5 μm, 4 wt% of silica ($SiO_2$), 2 wt% of calcia ($CaO_2$), and 2 wt% of magnesia (MgO); 12 parts by weight of butyral resin and 6 parts by weight of dibutyl phthalate (DBP) were added to the 100 parts by weight of the powder mixture; a slurry was made by mixing the powder mixture after the above addition in an organic solvent; and the green sheets were formed from the slurry by using a doctor blade. The thickness of the green sheets was adjusted so as to produce the ceramic substrate green sheet 70 with a 1 mm thickness, the ceramic cover green sheet 71 with a 0.2 mm thickness, the first ceramic layer green sheet 72 with a thickness of 0.8 mm, and the second ceramic layer green sheet 73 with a 0.8 mm thickness.

Electrically conductive layers 74 through 79 were printed in the form of thick film patterns, by using a platinum paste made by adding 7% of alumina ($Al_2O_3$) based on the amount of platinum. Of such conductive layers, electrodes 74 and 75 were for measuring the electric resistance of the above-mentioned gas-sensitive layer 31, and a heater layer 76 was for heating the gas-sensitive layer 31. End portions 77 through 79 were for applying an electric current to the heater layer 76 and extracting the output signal from the gas-sensitive layer 31.

In preparing the gas sensor 40, patterns for the electrodes 74, 75 and the heater layer 76 were at first printed on the ceramic substrate green sheet 70 together with their end portions 77 through 79 by using the platinum paste, a shown in FIG. 12A and FIG. 12B. Thereafter, platinum lead wires 81 through 83 with an outer diameter of 0.2 mm were disposed on the end portions 77 through 79 of the patterns respectively, as shown in FIG. 13A and FIG. 13B.

As shown in FIG. 14A and FIG. 14B, an opening 85 was bored, for instance by punching, through the ceramic cover green sheet 71 at such a position that, when the ceramic cover green sheet 71 with the opening 85 thus bored was overlaid in position on the ceramic substrate green sheet 70 so as to cover the entire pattern-printed surface of the latter sheet, the tip portions of the electrodes 74 and 75 were exposed to the outside through the opening 85. After being overlaid in the above manner, the ceramic cover green sheet 71 was joined to the ceramic substrate green sheet 70 by heating and pressing. In the illustrated embodiment, the lamination formed of the thus joined two green sheets 70 and 71 corresponded to the above-mentioned ceramic substrate 32 of FIG. 8. Gas-sensitive material 41 was deposited in the opening 85 so as to provide the above-mentioned gas-sensitive layer 31 of FIG. 8.

Referring to FIG. 15A and FIG. 15B, the first ceramic layer green sheet 72 was overlaid on the ceramic cover green sheet 71 of the above lamination and joined thereto by heating and pressing. A setback was provided in the first ceramic layer green sheet 72 so as to provide a protective staircase-like step 1c as shown in FIG. 15A. Thereafter, the second ceramic layer green sheet 73 with a central notch 86 at the edge facing the opening 85 was overlaid on and joined to the first ceramic layer green sheet 72 by heating and pressing while forming a setback relative to the latter green sheet as shown in FIG. 16A and FIG. 16B. Whereby, a positioning staircase-like step 1b was formed at that end of the second ceramic layer green sheet 73 which faces the opening 85. In this case, the green sheets 72 and 73 thus joined to the green sheets 71 corresponded to the above-mentioned first ceramic layer 33 and the second ceramic layer 34 of FIG. 8 respectively.

Thus, the printed patterns for the electrodes 74, 75 and the heater layer 76 were sandwiched between the green sheets 70 and 71, with the platinum lead wires 81 through 83 partially projecting to the outside of the thus joined green sheets 70 and 71 and with the tip portions of the electrodes 74 and 75 being exposed to the outside through the opening 85, and a green lamination with the staircase-like edge structure was formed by joining the ceramic layer green sheets 72 and 73 to the above green sheets 70 and 71 in the aforesaid manner. The green lamination was fired at 1,500° C. in air for two hours, so as to provide the ceramic substrate 32 carrying the ceramic layers 33 and 34 laminated thereon.

Figures 17A, 17B:
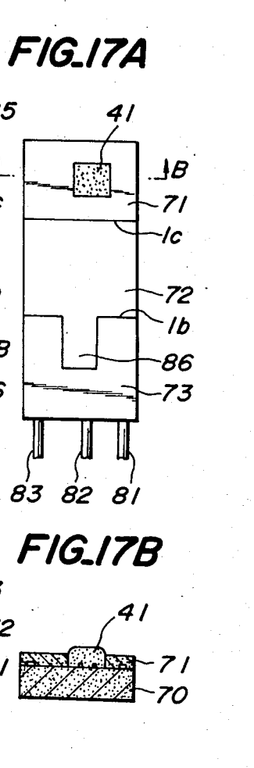

As shown in FIG. 17A and FIG. 17B, gas-sensitive material 41 was deposited on the fired ceramic substrate 32 through the opening 85 of its cover layer formed of the ceramic cover green sheet 71. To this end, a titania paste was prepared in the following manner; namely, 1 mole part of platinum black was mixed in 100 mole parts of titania ($TiO_2$) powder having a mean diameter of 1.2 μm; 3 wt% of ethyl cellulose based on the total of the powder mixture was added therein; and the mixture thus prepared was further mixed in BUTYL CARBITOL (a merchandise mark of 2-(2-butoxy ethoxy)ethanol) while controlling its viscosity so as to produce the titania paste having a viscosity of 300 poise.

The titania paste was applied to the opening 85 by the thick film techniques so as to fill up the opening 85 while ensuring tight contact of the tip portions of the electrodes 74 and 75 with the titania paste. The ceramic lamination with the titania paste applied thereof was fired at 1,200° C. in air for one hour, so that the gas-sensitive layer 31 was formed as overlaid on the ceramic substrate 32. Whereby, a sample of the gas sensor 40 according to the invention was completed. It should be noted here that the thickness of the first ceramic layer 33 made by firing the first ceramic layer green sheet 72 was thicker than the height of gas-sensitive element 31 from that surface of the ceramic substrate 32 which adjoined the first ceramic layer 33. In fact the above-mentioned height was less than 0.3 mm. Besides, the positioning staircase-like step 1b formed by the setback edge surface of the second ceramic layer green sheet 73 must not be linear but should be curved in the width direction of the ceramic substrate 32.

Figure 18A:
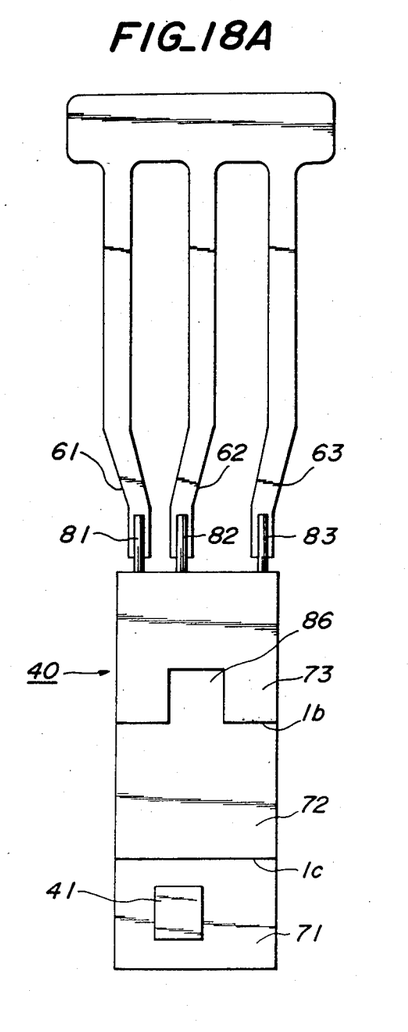
FIG. 18A is an explanatory diagram of the connections between lead wires and terminals.
Figure 18B:
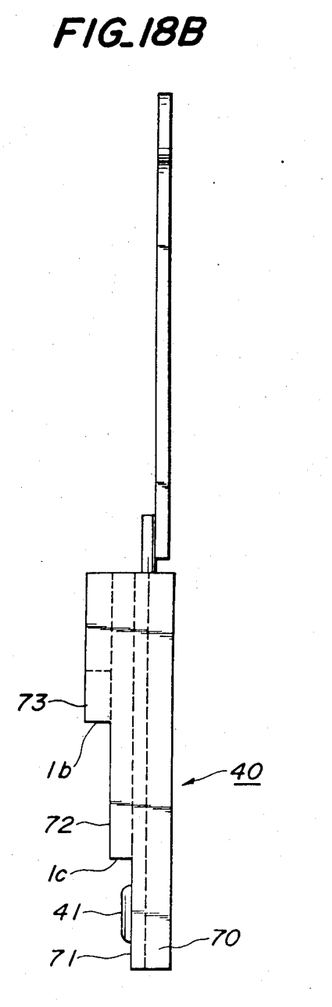
FIG. 18B is a side view of FIG. 18A.

The platinum lead wires 81 through 83 extending outwardly from the gas sensor 40 were connected to the terminals 61 through 63 respectively in a manner as shown in FIG. 18A. FIG. 18B shows a side view of the illustration of FIG. 18A. The terminals 61 through 63 were made by etching a 0.3 mm thick nickel plate without severing them from each other as shown in FIG. 18A. The terminals 61 through 63 were brought in contact with the platinum lead wires 81 through 83 respectively, and the portions in contact with each other were bonded by welding. The gas sensor 40 thus provided with the terminals was placed in the inner cylinder 44 carried by the housing body hardware 42 as shown in FIG. 10, so that the joint portions between the platinum lead wires 81 through 83 and the terminals 61 through 63 respectively were protected by the glass seal 47 fitted in the inner cylinder 44. Then, the three terminal 61 through 63 were severed from each other at suitable portions so as to povide the terminals of certain lengths.

As described in the foregoing, the gas sensor 40 according to the invention has two staircase-like steps; namely, a protective staircase-like step 1c at that end of the ceramic substrate 32 which carries the gas-sensitive layer 31, and a non-linear positioning staircase-like step 1b formed between the first ceramic layer 33 and the second ceramic layer 34. Thus, when a spacer 45 is mounted on the gas sensor 40 of the invention, the spacer 45 is readily positioned in a reliable and correct manner at the non-linear positioning staircase-like step 1b between the first ceramic layer 33 and the second ceramic layer 34 of the staircase-like edge structure as shown in FIG. 19. The ceramic layers 33 and 34 of the illustrated embodiment were made by using the green sheets 72 and 73 as explained above in detail.

Besides, that portion of the gas sensor 40 which engages the inside surface of the spacer 45 is thicker than the height of the gas-sensitive layer 31 from the bottom of the gas sensor 40 so that the inside hole of the spacer 45 is larger than the gas-sensitive-layer-carrying portion of the gas sensor 40 and the spacer 45 can be easily mounted on the gas sensor 40 without touching the gas-sensitive layer 31. Accordingly, the efficiency in the work of mounting the gas sensor 40 on the housing body hardware 42 is improved and the risk of harming the gas-sensitive layer 31 during such mounting is substantially eliminated.

In the case of the oxygen sensor which has been described above as an embodiment of the invention, a power source voltage for heating is applied across the lead wires 51 and 53 so as to heat up the heater layer 76 for activating the gas-sensitive layer 31. The oxygen concentration can be determined by measuring the electric resistance across the lead wires 52 and 53, and change of the oxygen concentration can be monitored by measuring variations in the above electric resistance.

As described in the foregoing, a gas sensor according to the invention has a protective staircase-like step 1c and a non-linear positioning staircase-like step 1b, and the protective step 1c is formed between a gas-sensitive-layer-carrying end of the substrate and a first ceramic layer overlaid on the substrate with a setback from the gas-sensitive layer, the first ceramic layer being thicker than the height of the gas-sensitive layer above the substrate, and the positioning step 1b is formed between that above first ceramic layer and a second ceramic layer overlaid on the first ceramic layer with a setback therefrom. Whereby, when the gas sensor is mounted on a housing or fixed to an object, the positioning of the gas sensor can be easily effected by using the step between the first ceramic layer and the second ceramic layer, so that the mounting or the fixing of the gas sensor can be carried out efficiently. Besides, the non-linear shape of the positioning staircase-like step 1b provides a high strength against mechanical shock.

Since the first ceramic layer is thicker than the height of the gas-sensitive layer over the ceramic substrate, when a spacer is used to facilitate the mounting of the gas sensor on a housing or the like, the spacer is prevented from coming in direct contact with the gas-sensitive layer and harming such gas-sensitive layer.

Further, the gas sensor of the invention has a thick end and a thin end with the gas-sensitive layer, and if its thick end is held by the housing or the like so as to extend the thin end into a measuring atmosphere, the heat capacity of the gas-sensitive portion is kept small for providing fast response by facilitating quick temperature rise of the gas-sensitive layer while ensuring steady holding of the gas sensor itself.

In short, a gas sensor according to the invention has a high strength against mechanical shock, and the conventionally experienced breakage of its substrate at a positioning staircase-like portion in case of inadvertent dropping is eliminated by making such staircase-like step non-linear in the width direction of the substrate.

Although the invention has been described with a certain degree of particularity, it is understood that the present disclosure has been made only by way of example and that numerous changes in details of construction and the combination and arrangement of parts may be resorted to without departing from the scope of the invention as hereinafter claimed.

What is claimed is:

1. A gas sensor comprising an elongated planar ceramic substrate, a gas-sensitive layer formed at one longitudinal end of the ceramic substrate, and a ceramic layer integrally overlaid on the ceramic substrate with a setback from the gas-sensitive layer so as to form a staircase-like step on the ceramic substrate, the staircase-like step of the ceramic layer being non-linear in width direction of the ceramic substrate with at least one first portion longitudinally extending toward the gas sensitive layer and at least one second portion not longitudinally extending toward the gas sensitive layer so that the length of the ceramic layer including the extended portion is longer than the length of the ceramic layer not including the extended portion, the extended end of said first portion of the staircase-like step being spaced from the gas-sensitive layer, whereby the ceramic substrate with the staircase-like step formed thereon has a high strength against mechanical shock.

2. A gas sensor as set forth in claim 1, wherein said gas sensor further comprises a heater layer secured to the ceramic substrate so as to heat the gas-sensitive layer.

3. The gas sensor according to claim 1, wherein said staircase-like step comprises two longitudinally extended portions located at opposite ends of the end of the ceramic layer nearest the gas sensitive layer and a notch which separates said extended portions.

4. The gas sensor according to claim 1, wherein said staircase-like step comprises a single longitudinally extended portion located near the center of the end of the ceramic layer nearest the gas sensitive layer and wherein the width of the extended portion does not extend for the entire width of said ceramic layer.

5. A gas sensor comprising an elongated planar ceramic substrate, a gas-sensitive layer formed at one longitudinal end of the ceramic substrate, a front ceramic layer integrally overlaid on the ceramic substrate in the proximity of but with a setback from the gas-sensitive layer so as to form a protective staircase-like step on the ceramic substrate, height of the protective staircase-like step from a boundary surface between the ceramic substrate and the front ceramic layer being higher than thickness of said gas-sensitive layer from said boundary surface, and a rear ceramic layer integrally overlaid on the ceramic substrate with a setback from the protective staircase-like step so as to form a positioning staircase-like step on the ceramic substrate, the height of the positioning staircase-like step being higher than said protective staircase-like step relative to said boundary surface, the positioning staircase-like step of the rear ceramic layer being curved in width direction of the ceramic substrate with at least one portion extending toward the gas-sensitive layer, whereby the ceramic substrate with the positioning staircase-like step formed thereon has a high strength against mechanical shock.

6. The gas sensor according to claim 5, wherein said positioning staircase-like step comprises two longitudinally extended portions located at opposite ends of the end of the rear ceramic layer nearest the gas sensitive layer and a notch which separates said extended portions.

7. The gas sensor according to claim 5, wherein said positioning staircase-like step comprises a single longitudinally extended portion located near the center of the end of the rear ceramic layer nearest the gas sensitive layer and wherein the width of the extended portion does not extend for the entire width of said rear ceramic layer.

8. The gas sensor according to claim 5, wherein the sensor further includes a heating layer.

9. A gas sensor comprising an elongated planner ceramic substrate, a gas-sensitive layer formed at one longitudinal end of the ceramic substrate, a first ceramic layer integrally overlaid on the ceramic substrate with a setback from the gas-sensitive layer so as to form a protective staircase-like step on the ceramic substrate, height of the protective staircase-like step from a boundary surface between the ceramic substrate and the first ceramic layer being higher than thickness of said gas-sensitive layer from said boundary surface, and a second ceramic layer integrally overlaid on the first ceramic layer with a setback from the protective staircase-like step of the first ceramic layer so as to form a positioning staircase-like step on the first ceramic layer, the positioning staircase-like step of the second ceramic layer being curved in width direction of the ceramic substrate with at least one portion extending toward the gas-sensitive layer, whereby the ceramic substrate with the positioning staircase-like step formed thereon has a high strength against mechanical shock.

10. The gas sensor according to claim 9, wherein said positioning staircase-like step of said second ceramic layer comprises two longitudinally extended portions located at opposite ends of the end of the second ceramic layer nearest the gas sensitive layer and a notch which separates said extensions.

11. The gas sensor according to claim 9, wherein said positioning staircase-like step of said second ceramic layer comprises a single longitudinally extended portion located near the center of the end of the second ceramic layer nearest the gas sensitive layer and wherein the width of the extended portion does not extend for the entire width of said second ceramic layer.

12. The gas sensor according to claim 9, wherein the sensor further includes a heating layer.

* * * * *